US008008511B2

(12) United States Patent
Pfeffer et al.

(10) Patent No.: US 8,008,511 B2
(45) Date of Patent: Aug. 30, 2011

(54) PROCESS FOR MODIFYING DRUG CRYSTAL FORMATION

(75) Inventors: Sabine Pfeffer, Weil am Rhein (DE); Dierk Wieckhusen, Binzen (DE)

(73) Assignee: Novartis AG, Basel (CH)

( * ) Notice: Subject to any disclaimer, the term of this patent is extended or adjusted under 35 U.S.C. 154(b) by 93 days.

(21) Appl. No.: 12/337,663

(22) Filed: Dec. 18, 2008

(65) Prior Publication Data

US 2009/0209639 A1 Aug. 20, 2009

Related U.S. Application Data

(63) Continuation of application No. 10/541,504, filed as application No. PCT/EP2004/000354 on Jan. 19, 2004, now abandoned.

(30) Foreign Application Priority Data

Jan. 20, 2003 (GB) .................................. 0301259.8

(51) Int. Cl.
*C07D 307/78* (2006.01)
(52) U.S. Cl. ....................................................... 549/310
(58) Field of Classification Search .................. 549/310; 514/469
See application file for complete search history.

(56) References Cited

U.S. PATENT DOCUMENTS

| 158,835 | A | 1/1875 | Erlin | |
|---|---|---|---|---|
| 3,183,263 | A | 5/1965 | Frump et al. | 260/534 |
| 3,187,039 | A | 6/1965 | Frump et al. | 260/534 |
| 3,352,906 | A | 11/1967 | Parkerson et al. | 260/534 |
| 3,770,390 | A | 11/1973 | Teot | 23/300 |
| 4,259,239 | A | 3/1981 | Sifniades et al. | |
| 4,533,506 | A | 8/1985 | Lahav et al. | |
| 5,531,922 | A | 7/1996 | Okinaka et al. | |

FOREIGN PATENT DOCUMENTS

| EP | 225 503 | 6/1987 |
|---|---|---|
| GB | 935 432 | 8/1963 |
| GB | 2145074 A | 3/1985 |
| GB | 97/38689 | 10/1997 |
| JP | 02006399 | 1/1990 |
| JP | 9209297 A | 8/1997 |
| WO | WO 95/07902 | 3/1995 |
| WO | 99/67236 | 12/1999 |
| WO | WO 99/67236 | 12/1999 |
| WO | WO9967236 | * 12/1999 |
| WO | 2004/064806 | 8/2004 |

OTHER PUBLICATIONS

Bazhal et al., "Role of Oscillation Mechanism of Recrystallization in the Distribution of a Microcomponent Between Liquid and Solid Phases", *Radiokhimiya*, vol. 20, No. 4, pp. 481-484 (1978)—English Abstract.
Berkovitch-Yellin et al., "Crystal Morphology Engineering by 'Tailor-Made' Inhibitors: A New Probe to Fine Intermolecular Interactions", *J Am Chem Soc*, vol. 107, No. 11, pp. 3111-3122 (1985).
Buckley, "The Crystallization of Potash Alum and the Effect of Certain Added Impurities on Its Habit", *Z Kirst*, vol. 73, pp. 443-464 (1930)—English Abstract.
Chan and Gonda, "Serendipitous Preparation of Crystals of Methotrexate and Attempts to Modify Its Crystal Habit", *J Cryst Growth*, vol. 94, No. 2, pp. 488-498 (1989).
Honigmann, "Modification of the Habit of Sodium Chloride Crystals in Saturated Solution Under the Influence of Temperature Oscillations", *Z Elektrochem*, vol. 56, pp. 342-345 (1952)—English Abstract.
Kim and Ulrich, "Purification of Crystalline Layers by Controlling the Temperature Gradient", *Powder Techol*, vol. 121, pp. 81-87 (2001).
Nývlt and Ulrich, "Admixtures in Cyrstallization", *VCH*, pp. 1-74 (Dec. 1994).
Skrivanek and Zacek, "Crystallization of Compounds Forming Needle Shaped Crystals", *Krist Tech*, vol. 10, No. 11, pp. 1141-1145 (1971)—English Abstract.
Weissbuch, Popovitz-Biro, Lahav and Leiserowitz, "Understanding and Control of Nucleation, Growth, Habit, Dissolution and Structure of Two- and Three-Dimensional Crystals Using 'Tailor-Made' Auxiliaries", *Acta Cryst*, Section B51, No. 2, pp. 115-148 (1995).
Wireko et al., "Effect of Solvent on the Growth of Organic Crystals. 1. The Riddle of α-Resorcinol", *J Phys Chem*, vol. 91, No. 2, pp. 472-481 (1987).

* cited by examiner

*Primary Examiner* — Nizal Chandrakumar
(74) *Attorney, Agent, or Firm* — Leslie Fischer; David R. Kurlandsky

(57) ABSTRACT

A process for modifying the crystal habit of acicular drug substances, crystals obtained by such a process, and particular crystal forms or modifications of mycophenolic acid or mycophenolate sodium are provided, as well as pharmaceutical compositions comprising the crystals, methods of treatment and uses thereof.

3 Claims, 12 Drawing Sheets

PROCESS FOR MODIFYING DRUG CRYSTAL FORMATION

This is a continuation of Application No. 10/541,504 filed on Jul. 8, 2005, which is a National Stage of International Application No. PCT/EP04/000354 filed on Jan. 19, 2004, which claims benefit of Great Britain Application No. 0301259.8 filed on Jan. 20, 2003, the entire disclosures of which are hereby incorporated by reference.

The present invention relates to a process for modifying the crystal habit of acicular drug substances, to the resulting crystallized drug substances and to pharmaceutical compositions comprising the same.

Industrial crystallization inter alia aims at producing crystals of a defined quality such as shape, particle size and/or bulk density.

Usually, crystals grow in three directions, length, width and height. Some crystals however, have one or two preferred growth directions. For example, acicular substances e.g. crystals in the form of needles, rods or capillaries, have a preferred crystal growth in one direction. The ratio between the length and the width of a crystal, the so-called aspect ratio, is significantly higher than 1:1 for acicular crystals; the higher the aspect ratio, the longer the crystal needles, rods or capillaries.

Acicular crystals often display poor processability, inefficient processing, e.g. for the manufacture of galenical formulations, tend to have a poor flowability and/or a low bulk density, e.g. a bulk density of below about 200 kg/m$^3$. Thus the formulation of e.g. tablets comprising said crystalline material may result in e.g. low mechanical stability of the formulation, an undesirably large dosage form and/or may require special compression methods.

It is thus desirable to modify the crystal habit, i.e. the relative rates of the growth of the crystal in different directions, of acicular crystals. This may be achieved by retarding the crystal growth of the preferred growth direction, and/or enhancing the growth of the less preferred growth directions. Preferably, such a process does not have an effect on polymorphism.

Retardation of a crystal growth direction may be achieved e.g. by additives that act as competitive agents and adsorb onto the fastest growing face and thus hinder crystal growth in this direction. In ice-cream technology this method is very well established. Carrageenan is added to inhibit needlelike growth of water crystals in order to avoid an "icy" taste. Another example is the addition of additives to diesel fuel in winter that prevents paraffin crystals from growing in long needles that would clog the fuel lines. In case of a drug substance, the addition of an additive is however problematic.

Solvents have been used to influence the crystal habit of the solute, however, with an unsatisfactory effect.

Increase of particle size of acicular crystals has been achieved by temperature oscillation. When using temperature oscillation, crystals may however grow bigger without changing or without changing substantially the crystal habit.

Temperature oscillation has been combined with sonication to modify the crystal habit of crystalline needles. The sonication limits the growth of the length of the needles by breaking them. Therefore, this process is not convenient for industrial crystallization as it may cause e.g. severe noise and abrasion of equipment.

Thus, there is a need for a crystallization process for acicular drug substances leading to improved crystal growth, particularly applicable to industrial manufacture.

Applicants have now found a process for modifying the crystal habit of acicular crystals of a drug substance yielding a crystalline drug substance with improved bulk density and/ or a reduced mean aspect ratio. Additional steps, such as sonication or application shear forces with high-shear mixers or homogenizers, for breaking the crystals, are not required.

The drug substance obtained in accordance with the process of the invention preferably has a bulk density above about 200 kg/m$^3$, e.g. about 300 to about 600 kg/m$^3$, and/or the mean aspect ratio is smaller than about 10:1, e.g. between about 1:1 and about 10:1, e.g. about 5:1, e.g. about 2:1.

Accordingly, the present invention provides a process for modifying the crystal habit of acicular drug substances comprising suspending said crystals in a solvent system having an effect on the crystal habit and subjecting said suspension to a temperature oscillation. In another embodiment, the present invention provides a process for recrystallization of acicular drug substances comprising suspending said crystals in a solvent system having an effect on the crystal habit and subjecting said suspension to a temperature oscillation. The present invention further provides a process for producing crystals of an acicular drug substance having a bulk density of above about 200 kg/m$^3$, preferably about 300 to about 600 kg/m$^3$, and/or a mean aspect ratio of below about 10:1, more preferably below about 5:1, even more preferably below about 2:1. The particle size of the crystals may be increased by said process.

The solvent system having an effect on the crystal habit retards the crystal growth of the preferred growth direction and/or enhances the crystal growth of the less preferred crystal faces. The effect of the solvent system on the crystal habit may be small and may be enhanced by temperature oscillation.

By "solvent system" is meant a solvent or solvent mixture comprising optionally an additive. The solvent system may be removed at the end of the crystallization process, e.g. evaporated when drying the processed crystals; preferably it is removed.

Typically, the solvent system is chosen in a way that chemical or physical interactions, e.g. hydrogen bonds or ionic bonds, between the solvent, solvents and/or additive and the crystal face may be formed. Steric effects may also have to be considered to allow the solvent-crystal or additive-crystal interaction. E.g. in the case of an ionic compound, preferably a polar solvent or additive is chosen, and in case of hydrogen-binding compounds, preferably a hydrogen bond-donor or acceptor solvent or additive is chosen.

Suitable solvents are those known to the skilled person, such as a) a polar protic solvent such as an alkanol e.g. a $C_{1-6}$ alkanol, preferably a $C_{1-4}$ alkanol, wherein the alkyl radical may be linear or branched such as methanol, ethanol or isopropanol; or a cycloalkanol, e.g. cyclohexanol; water; an organic acid e.g. a $C_{1-8}$ carboxylic acid, e.g. acetic acid, b) a dipolar aprotic solvent such as an ester e.g. a carboxylic acid ester e.g. isopropyl acetate, ethyl acetate; a ketone e.g. acetone; an ether e.g. diethyl ether, methyl t-butyl ether; an amide e.g. formamide, dimethylformamide; dimethylsulfoxide; a nitrile e.g. acetonitrile, c) a non-polar solvent such as an alkane e.g. hexane or heptane, a cycloalkane, e.g. cyclohexane; or an aromatic hydrocarbon, e.g. toluene or xylene; or d) any mixture thereof.

Suitable additives are those known to the skilled person e.g. those described in J. Nyvlt and J. Ulrich "Admixtures in Crystallization" (VCH Weinheim, 1995), the contents thereof being incorporated herein by reference. The additive may be present in an amount of about 1 ppm to about 10% by weight of the drug substance.

The crystalline suspension is prepared by methods known to a skilled person.

Typically, the crystals are dispersed in a solvent system so that a significant amount of drug substance, e.g. less than 70% by weight, e.g. less than 50% by weight, e.g. about 10 to about 30% by weight of drug substance, dissolves upon heating and recrystallizes upon cooling.

The temperature oscillation is performed by heating and cooling the crystalline suspension to predetermined temperature, conveniently under stirring. The parameters for the temperature oscillation depend upon the nature of the solvent or solvent mixture, the nature of the crystals, the desired particle size and/or desired bulk density and may be optimized using standard tests. The particle size of the processed crystals may be assessed e.g. by microscopy.

The mean temperature and the temperature amplitude may be chosen to bring a significant amount of drug substance into solution, e.g. between 10 and 30% of drug substance. Typically, the temperature amplitude may be about e.g. about ±1° C. to about ±20° C., e.g. about ±5° C. to ±10° C. The temperature amplitude may be different or the same for each oscillation, preferably it is the same for each oscillation.

The temperature oscillation curve may be in the form of approximately a sinus curve with a temperature holding step or approximately a zig-zag curve, i.e. a curve comprising a substantially linear heating step and a substantially linear cooling step. Preferably, the temperature oscillation curve is approximately a zig-zag curve, more preferably with the same temperature amplitude. Typically, the oscillation starts with heating of the suspension.

In order to avoid total process time of several days, e.g. of more than two days, heating time and cooling time may be each e.g. about 20 to about 120 minutes, e.g. about 80 minutes. Between heating and cooling, there may be a temperature holding step, e.g. of a duration of about 5 min. Preferably, the heating time may be shorter than the cooling time, e.g. the heating time may be about 25 minutes and the cooling time may be about 80 minutes.

In general, the higher the number of oscillations, the more the aspect ratio tends towards 1:1 and the larger the particles. Practically, the number of oscillations may be about 6 to about 16, e.g. about 8 to about 10, oscillations.

Finally, the suspension is cooled to a temperature below about 23° C. in order to reduce the solubility of the crystals in the solvent system. Addition of a further solvent wherein the crystals have a low solubility may increase the yield of the process. Finally, the crystals are filtered and dried. Drying of the crystals, e.g. in a rotary dryer, may further increase the bulk density.

Crystals of the acicular drug substance preferably have a mean aspect ratio of greater than 2:1, more preferably greater than 5:1, most preferably greater than 10:1 before the process of the invention is carried out. In particular, the present invention relates to acicular drug substances such as mycophenolic acid or a mycophenolate salt in acicular form, preferably mycophenolate salt. The acicular drug substance may be one of the polymorphic forms of mycophenolate sodium described below. Preferably the acicular drug substance is in the form of a crystal modification of mycophenolate sodium anydrate (modification A), mycophenolate sodium hydrate or the hemisalt of anhydrous mycophenolate sodium as described at A, B or C below.

The mycophenolic acid or mycophenolate salt is most preferably in an amount of about 95%, preferably about 98%, even more preferably about 100%, in the form of its anhydrate. Examples of mycophenolate salts include e.g. cationic salts of mycophenolic acid, e.g. of alkali metals, especially the sodium salt. Preferred salt is the mono-sodium salt.

The crystals obtained by the process of the invention have an aspect ratio of about 10:1 to about 1:1, e.g. about 5:1 to about 2:1, and/or a bulk density of above about 200 kg/m$^3$, e.g. of between about 300 and about 600 kg/m$^3$, e.g. 500 kg/m$^3$.

In accordance with the foregoing the present invention further provides crystals of mycophenolic acid or a mycophenolate salt in acicular form with an aspect ratio of about 10:1 to 1:1 and/or a bulk density of above about 200 kg/m$^3$, e.g. prepared by the process of the invention described herein. A preferred solvent system is a mixture of polar protic solvents, e.g. a mixture of water and an alkanol such as indicated above. A typical temperature oscillation is at a mean temperature of 42-47° C. with an amplitude of ±5-7° C.

In a further aspect, the present invention relates to particular crystal forms or modifications of mycophenolic acid or mycophenolate sodium, having properties as described below.

A. In one embodiment, the invention relates to a crystal modification A (Mod A) of mycophenolate sodium anhydrate. The single crystal structure of modification A could be solved. Mod A crystallizes in the monoclinic space group P2$_1$/c. The cell dimension and volume are shown below. In the following dimensions are in Å, volume in Å$^3$.

| | |
|---|---|
| space group: | P2$_1$/c |
| a: | 16.544 (4) |
| b: | 4.477 (1) |
| c: | 21.993 (3) |
| β: | 92.14 (1) |
| V: | 1627.8 (6) |
| Z: | 4 |
| cal. Density: | 1.397 g/cm$^3$ |

Differential Scanning Calorimetry (DSC)

The DSC curve is measured in pans with a heating rate of 10 K/min for identity. The DSC curve of modification A shows an endothermic peak at about 191° C. due to the melting process of the drug substance (corrected onset temperature with indium, instrument: Perkin Elmer DSC-7).

Thermogravimetry

The thermogravimetry curve of the anhydrous mycophenolate sodium Mod A shows no significant amount of loss on mass during heating (instrument: Mettler TGA850).

X-Ray Powder Diffraction

The X-ray powder diffraction pattern of Mod A is shown in FIG. 1. The calculated X-ray powder pattern using the single crystal structural data is in agreement with the experimental XRPD (instrument: Scintag XDS, calculations are performed e.g. with CERIUS 2 software package (MSI)).

Morphology

Mod A crystals are acicular, columnar shaped.

Infra-Red Spectrum

The following infra-red absorption bands are typical for anhydrous mycophenolate sodium, modification A

| | |
|---|---|
| 2927, 2863 | C—H aliphatic |
| 1718 | C=O lactone |
| 1616 | C=C olefinic/aromatic |
| 1572 | C=O carboxylic acid |
| 1451 | CH$_2$, CH$_3$ |
| 1372 | CH$_3$ |

| | |
|---|---|
| 1267 | C—O phenol |
| 832 | C—H o.o.p. trisubstituted olefin |

B. In a further embodiment, the invention relates to a crystal modification of mycophenolate sodium hydrate having properties as described below.

Differential Scanning Calorimetry (DSC)

The DSC curve is measured in normal closed and tightly closed pans with a heating rate of 10K/min for identity. The DSC curve of mycophenolate sodium hydrate shows several endothermic peaks with both pan types and finally a peak about 191° C. corresponding to the melting process of mycophenolate sodium Mod A (instrument: Perkin Elmer DSC-7)

Thermogravimetry

The thermogravimetry curve of mycophenolate sodium hydrate shows a loss on mass during heating up to about 150° C. of about 5%, corresponding to a monohydrate (instrument: Mettler TGA850).

X-Ray Powder Diffraction

The X-ray powder diffraction pattern of mycophenolate sodium hydrate is shown in FIG. 2. The X-ray powder pattern can clearly be distinguished from the diffraction pattern of Mod A (instrument: Scintag XDS).

Morphology

The crystals of the hydrate are needle like, acicular shaped particles with a length of 20 to 600 μm.

Temperature Controlled X-Ray Diffraction of Hydrate Form

The crystalline hydrate is heated on the XRPD sample holder under 0% r.h. and the XRPD pattern recorded at different temperatures (shown in FIG. 3). A change of the X-ray powder pattern is obtained while heating into the anhydrous crystalline Mod A at 184° C. Between 30° C. and 184° C. under these conditions, two further crystalline forms which are very similar to the hydrate regarding the XRPD pattern are obtained. This result corresponds very well to the DSC curve.

C. In a further embodiment, the invention relates to a crystal modification of the hemisalt of mycophenolate sodium (anhydrous) having properties as described below.

The single crystal structure of the hemisalt of mycophenolate sodium could be solved. It crystallizes in the triclinic space group P-1. The cell dimension and volume are shown below.

| space group: | P-1 |
|---|---|
| a: | 11.172(6) |
| b: | 12.020(6) |
| c: | 13.441(2) |
| α: | 73.09(7) |
| β: | 71.79(6) |
| γ: | 84.63(6) |
| V: | 1641(2) |
| Z: | 2 |

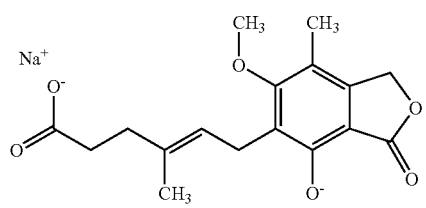

| space group: | P-1 |
|---|---|

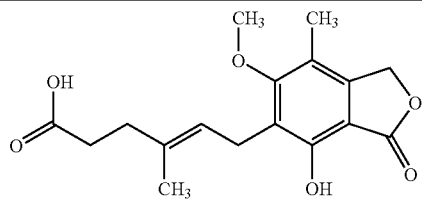

Differential Scanning Calorimetry (DSC)

The DSC curve is measured in pans with a heating rate of 10K/min for identity. The DSC curve of mycophenolate sodium adduct (hemisalt) shows an endothermic peak at about 158° C. due to the melting process of the substance (instrument: Perkin Elmer DSC-7).

Thermogravimetry

The thermogravimetry curve of mycophenolate sodium adduct (hemisalt) shows no significant amount of loss of mass during heating up to the melting of the substance (instrument: Mettler TGA850).

X-Ray Powder Diffraction

The X-ray powder diffraction pattern of mycophenolate sodium adduct (hemisalt) is shown in FIG. 4. The calculated X-ray powder pattern using the single crystal structural data is in agreement with the experimental XRPD (instrument: Scintag XDS).

Morphology

The crystals of the hemisalt (adduct) have a acicular, columnar and lath shaped morphology with a length between 20 and 200 μm and a width between 5 and 50 μm.

D. In a further embodiment, the invention relates to a crystal modification of mycophenolate sodium methanol solvate having properties as described below.

The single crystal structure of the methanol solvate of mycophenolate sodium could be solved. It crystallizes in the triclinic space group P-1. The cell dimension and volume are shown below.

Crystallographic space group: P-1, Z=2, V=976.3

| Cell dimension: | a: 7.761 | α: 109.96° |
|---|---|---|
| | b: 9.588 | β: 95.99° |
| | c: 14.094 | γ: 83.05° |

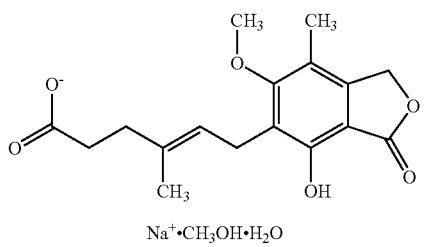

Na$^+$·CH$_3$OH·H$_2$O

Differential Scanning Calorimetry (DSC)

The DSC curve is measured in pans with a heating rate of 10K/min for identity. The DSC curve of ERL080 methanol solvate shows an endothermic peak at about 66° C. due to the melting process of the methanol solvate followed by small additional endothermic peaks up to a transformation to mycophenolate sodium, Mod A and the corresponding endothermic melting peak at about 188° C. (instrument: Perkin Elmer DSC-7).

Thermogravimetry

The thermogravimetry curve of the methanol solvate shows a significant amount of loss on mass during heating of about 7.4%. (instrument: Mettler TGA850)

X-Ray Powder Diffraction

The X-ray powder diffraction pattern of mycophenolate sodium methanol solvate is shown in FIG. 5. The calculated X-ray powder pattern using the single crystal structural data is in agreement with the experimental XRPD (instrument: Scintag XDS).

Morphology

The crystals of the methanol solvate are mostly plate shaped aggregates of columnar shaped particles with a diameter between 100 and 200 μm.

E. In a further embodiment, the invention relates to a crystal modification of mycophenolate sodium methanol solvate II having properties as described below.

The single crystal structure of the methanol solvate II of mycophenolate sodium could be solved. It crystallizes in the triclinic space group P-1. The cell dimension and volume are shown below.

| Crystallographic space group: | P-1, Z = 2, | V = 996.4 |
|---|---|---|
| Cell dimension: | a: 9.179 | α: 113.27° |
| | b: 10.724 | β: 101.76° |
| | c: 12.098 | γ: 104.44° |

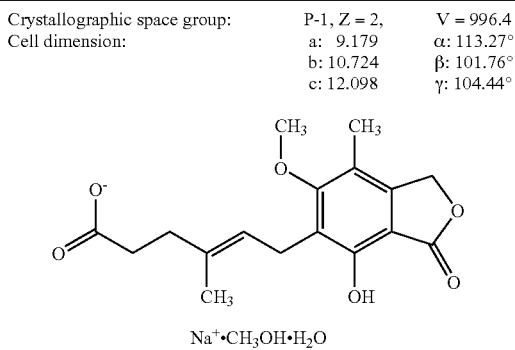

Na⁺·CH₃OH·H₂O

F. In a further embodiment, the invention relates to a crystal modification of mycophenolate disodium salt, monohydrate having properties as described below.

Differential Scanning Calorimetry (DSC)

The DSC curve is measured in pans with a heating rate of 10K/min for identity. The DSC curve of mycophenolate disodium salt, monohydrate shows several endothermic peaks up to the melting of the substance in tightly closed pans and only one endothermic peak at about 179° C. in normal closed pans (Perkin Elmer DSC-7, vsp pans).

Thermogravimetry

The thermogravimetry curve of mycophenolate disodium salt, monohydrate shows a loss on mass during heating of about 5% up to about 250° C. (instrument: Mettler TGA850).

X-Ray Powder Diffraction

The X-ray powder diffraction pattern of mycophenolate disodium salt, monohydrate is shown in FIG. 6. The X-ray powder diffraction pattern of the disodium salt can clearly be distinguished from the X-ray powder pattern of Mod A. (instrument: Scintag XDS).

Morphology

The crystals of the disodium salt monohydrate are lath shaped, light breakable particles with riled surfaces.

G. In a further embodiment, the invention relates to a crystal modification of mycophenolate disodium salt, pentahydrate having properties as described below.

The single crystal structure of the mycophenolate disodium salt, pentahydrate could be solved. It crystallizes in the monoclinic space group. The cell dimension and volume are shown below.

| Crystallographic space group: | P 2₁/c, Z = 4, | V = 2128 |
|---|---|---|
| Cell dimension: | a: 14.495 | β: 97.15° |
| | b: 17.613 | |
| | c: 8.401 | |

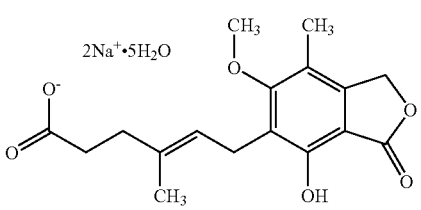

2Na⁺·5H₂O

After storage of the di-sodium salt monohydrate for 4 weeks at 40° C./75% r.h. in open ampoules, it changes to the di-sodium salt II pentahydrate. This is the only material obtained beside the single crystals. The identification of the pentahydrate is done using the single crystal structural data.

Thermogravimetry

The thermogravimetry curve of di-sodium salt II pentahydrate shows a significant amount of loss on mass during heating of about 19.8%. (instrument: Mettler TGA850)

X-Ray Powder Diffraction

The X-ray powder diffraction pattern of di-sodium salt II pentahydrate is shown in FIG. 7. The calculated X-ray powder pattern using the single crystal structural data is in agreement with the experimental XRPD (instrument: Scintag XDS).

H. In a further embodiment, the invention relates to a crystal modification of mycophenolic acid having properties as described below.

The single crystal structure of mycophenolic acid (salt free form of mycophenolate sodium) could be solved. It crystallizes in the triclinic space group P-1. The cell dimension and volume are shown below.

| Crystallographic space group: P-1, Z = 2, V = 796.3 | | |
|---|---|---|
| Cell dimension: | a: 7.342 | α: 102.70° |
| | b: 9.552 | β: 90.89° |
| | c: 11.643 | γ: 90.74° |

Differential Scanning Calorimetry (DSC)

The DSC curve is measured in pans with a heating rate of 10 k/min for identity. The DSC curve of mycophenolic acid shows an endothermic peak at about 143° C. due to the melting process of the substance (instrument: Perkin Elmer DSC-7).

Thermogravimetry

The thermogravimetry curve of mycophenolic acid shows no significant amount of loss on mass during heating up to the melting of the substance (instrument: Mettler TGA850).

X-Ray Powder Diffraction

The X-ray powder diffraction pattern of mycophenolic acid is shown in FIG. 8. The calculated X-ray powder pattern using the single crystal structural data is in agreement with the experimental XRPD (instrument: Scintag XDS).

Morphology

The crystals of mycophenolic acid are irregular shaped with adhesive particles with a length of <50 to >400 μm.

I. In a further embodiment, the invention relates to a crystal modification of mycophenolate sodium hydrate Form B (hydrate heated to 85° C.) having properties as described below.

Form B is produced by heating the hydrate on the X-ray sample holder to about 85° C. and then cooling the substance down to room temperature. The X-ray pattern at 85° C. and after subsequent cooling to room temperature (shown in FIG. 9) correspond to each other (instrument: Scintag).
Differential Scanning Calorimetry (DSC)

The DSC curve is measured in pans with a heating rate of 10K/min for identity. The DSC curve shows three endothermic peaks. The final endothermic peak corresponds to the melting of mod A. (instrument: Perkin Elmer DSC-7).
Thermogravimetry The thermogravimetry curve of Form B shows a loss on mass during heating of about 1%. (instrument: Mettler TGA850)
X-Ray Powder Diffraction The X-ray powder diffraction pattern of Form B is shown in FIG. 10 (instrument: Scintag XDS).

J. In a further embodiment, the invention relates to a crystal modification of mycophenolate sodium hydrate Form C (hydrate heated to about 155° C.) having properties as described below.

The Form C is produced by heating the hydrate on the X-ray sample holder to about 155° C. and then cooling the substance down to room temperature. The X-ray pattern at 155° C. and after subsequent cooling to temperature (shown in FIG. 11) correspond to each other (instrument: Scintag)
Differential Scanning Calorimetry (DSC)

The DSC curve is measured in pans with a heating rate of 10K/min for identity. The DSC curve of Form C shows two endothermic peaks: melting of Form C transition to Mod A and then melting ($2^{nd}$ endotherm) of Mod A. (instrument: Perkin Elmer DSC-7).
Thermogravimetry The thermogravimetry curve of Form C shows a loss on mass during heating of about 0.2%. (instrument: Mettler TGA850)
X-Ray Powder Diffraction The X-ray powder diffraction pattern of Form C is shown in FIG. 12 (instrument: Scintag XDS).

In further embodiments, the invention relates to pharmaceutical preparations comprising one or more of the above crystal modifications, e.g. alone or in a mixture comprising two or more of the above crystal modifications. Preferably the preparations comprise one of the crystal modifications in greater than 90%, more preferably greater than 95%, most preferably greater than 99% polymorphic purity, e.g as as determined by X-ray powder diffraction, DSC and IR spectrum. The invention also relates to the essentially pure form of each of the above crystal forms.

The various crystal modifications may be prepared by crystallization or recrystallization of any forms or mixtures of mycophenolic acid or mycophenolate sodium in a solution comprising water and/or an appropriate solvent. Modification A may be formed e.g. by crystallization of mycophenolate sodium from isopropanol. The hydrate form may be produced by dissolving mycophenolate sodium in methanol, adding aqueous sodium hydroxide and precipitating this solution in isopropanol. Heating the hydrate form to 85 or 155° C. leads to the formation of forms B and C respectively. The hemi-salt may be obtained by crystallization of mycophenolate sodium from water, preferably at pH 4 to 6. If the pH is lowered to below 2, the free acid form may be obtained. Methanol solvate forms may be obtained by crystallization of mycophenolate sodium from a mixture of methanol and water. Disalt forms may be obtained by crystallization from an aqueous solution of mycophenolate sodium, preferably containing an increased concentration of sodium ions and at a pH greater than 8.

Crystals in the form of one of the modifications described above at A to J, as well as crystals obtained by the modifying or recrystallizing processes of the present invention are referred to henceforth as "crystals of the invention". The crystals of the invention may be formulated for administration in any convenient way, e.g. in the form of tablets.

Tablets may be obtained e.g. by granulation of the crystals of the invention followed by compression. Tablets comprising crystals of the invention have an improved hardness, e.g. a hardness of about 130N to about 160N. The abrasion is less than about 0.5%, e.g. less than about 0.3%. Tablets may be coated tablets, e.g. enteric coated tablets. Suitable coating material comprises, e.g. hydroxypropyl methylcellulose phthalates, e.g. HPMCP HP50, and optionally pigments, e.g. iron oxide, indigotine, e.g. indigotine lake, and/or titanium dioxide.

Tabletting procedures which may be used may be conventional or known in the art or based on such procedures e.g. those described in L. Lachman et al. The Theory and Practice of Industrial Pharmacy, 3rd Ed, 1986, H. Sucker et al, Pharmazeutische Technologie, Thieme, 1991, Hagers Handbuch der pharmazeutischen Praxis, 4th Ed. (Springer Verlag, 1971) and Remington's Pharmaceutical Sciences, 13th Ed., (Mack Publ., Co., 1970) or later editions.

Accordingly, in another aspect, the present invention provides a pharmaceutical composition, e.g. in the form of tablets, comprising crystals of the invention, and a pharmaceutically acceptable carrier.

In another aspect, the present invention provides drug substance crystals of the invention for use as a pharmaceutical or in the preparation of a pharmaceutical composition for use in any method described in the art for said drug substance. Furthermore, the present invention provides the use of crystals and the pharmaceutical compositions of the invention for the preparation of a medicament for the treatment of any condition known therefore and described in the art.

The compositions of the invention comprising mycophenolic acid or a mycophenolate salt are useful as immunosuppressants as indicated by standard tests. The activity and characteristics of the compositions of the invention may be indicated in standard clinical trials or animal test as described e.g. in WO 97/38689, the content of which is incorporated herein by reference.

The pharmaceutical compositions of the invention comprising mycophenolic acid or mycophenolate salt are useful as immunosuppressants and in particular for the following conditions:

a) Treatment and prevention of native or transgenic organ, tissue or cellular allograft or xenograft transplant rejection, e.g. for the treatment of recipients of e.g. heart, lung, combined heart-lung, liver, kidney, pancreatic, skin, pancreatic islet cell, neural cell or corneal transplant; including treatment and prevention of acute rejection; treatment and prevention of hyperacute rejection, e.g. as associated with xenograft rejection; and treatment and prevention of chronic rejection, e.g. as associated with graft-vessel disease. The compositions of the invention are also indicated for the treatment and prevention of graft-versus-host disease, such as following bone marrow transplantation.

b) Treatment and prevention of autoimmune disease, e.g. immune-mediated disease and inflammatory conditions, in particular inflammatory conditions with an etiology including an immunological component such as arthritis (for example rheumatoid arthritis, arthritis chronica progrediente and arthritis deformans) and rheumatic diseases. Specific immune-mediated disease for which the compositions of the invention may be employed include, autoimmune hematological disorders, including, but not limited to hemolytic anaemia, aplastic anaemia, pure red cell anaemia and idiopathic thrombocytopenia), systemic lupus erythematosus, polychondritis, sclerodoma, Wegener granulosis, dermatomyositis, polymyositis, chronic active hepatitis, primary biliary cirrhosis, myasthenia gravis, psoriasis, Steven-Johnson syndrome, pemphigus, idiophatic sprue, inflammatory bowel disease (including e.g. ulcerative colitis and Crohn's disease), endocrine opthalmophathy, Graves disease sarcoidosis, multiple sclerosis, juvenile diabetes (diabetes mellitus type I), non-infectious uveitis (anterior and posterior), keratoconjunctivitis sicca and vernal keratoconjunctivitis, interstitial lung fibrosis, psoriatic arthritis, vasculitis, glomerulonephritides (with and without nephrotic syndrome, e.g. including idiophatic nephrotic syndrome or minimal change nephropathy) and juvenile dermatomyositis.

For the above uses the required dosage will of course vary depending on the drug substance used, the mode of administration, the particular condition to be treated and the effect desired.

Accordingly, the present invention further provides a method for treating and/or preventing native or transgenic organ, tissue or cellular acute or chronic allograft or xenograft transplant rejection or graft-versus-host diseases, or treating and/or preventing an autoimmune disease, e.g. as disclosed above, in a subject, such as a human or other animal subject, comprising administering to the subject an effective amount of a composition comprising crystals of the invention of mycophenolic acid or a mycophenolate salt.

Figure 1:
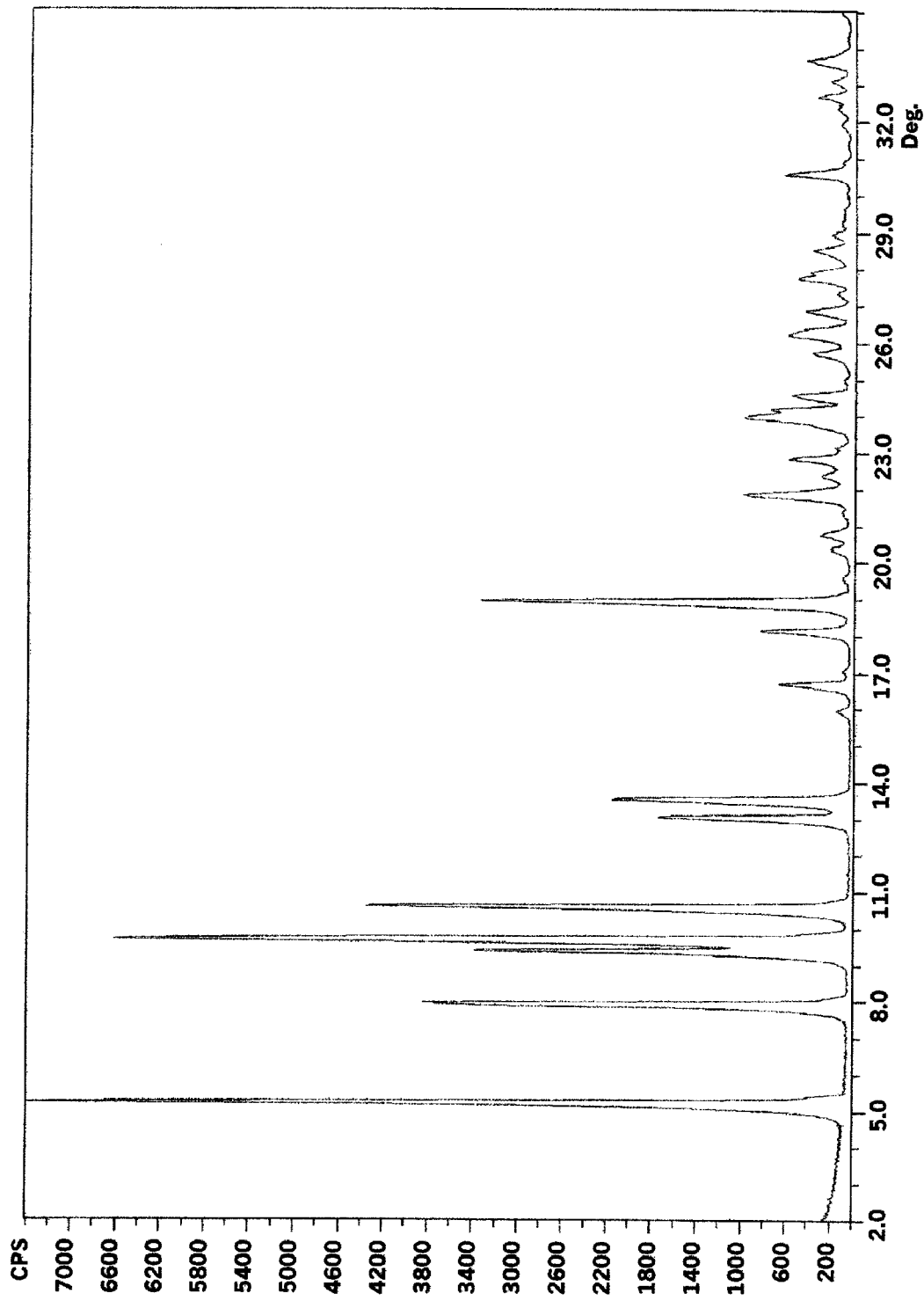
FIG. 1 shows the X-ray powder diffraction pattern of anhydrous mycophenolate sodium modification A.
Figure 2:
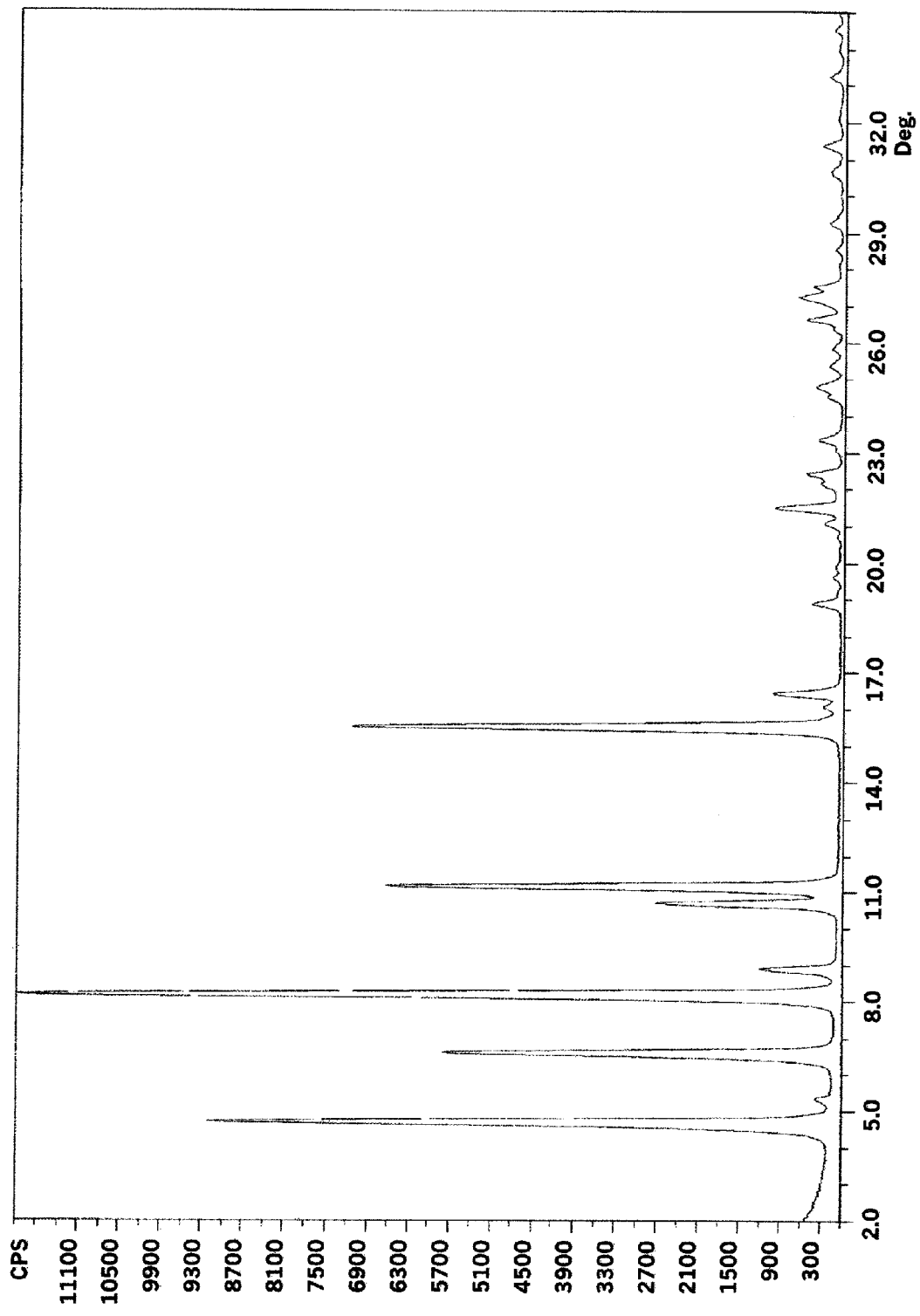
FIG. 2 shows the X-ray powder diffraction pattern of mycophenolate sodium hydrate.
Figure 3:
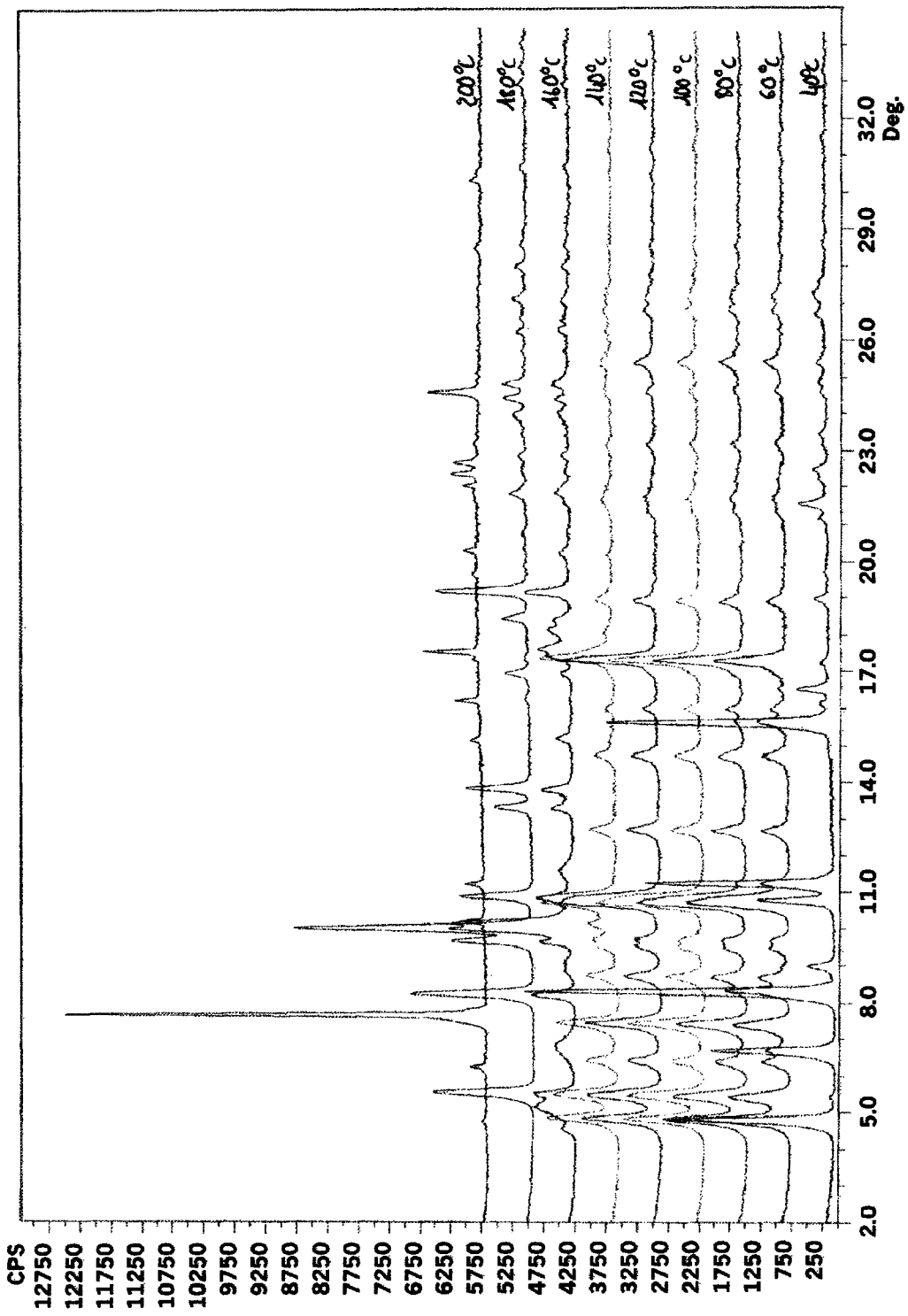
FIG. 3 shows XRPD pattern recorded at different temperatures when the crystalline hydrate is heated on the XRPD sample holder under 0% relative humidity.
Figure 4:
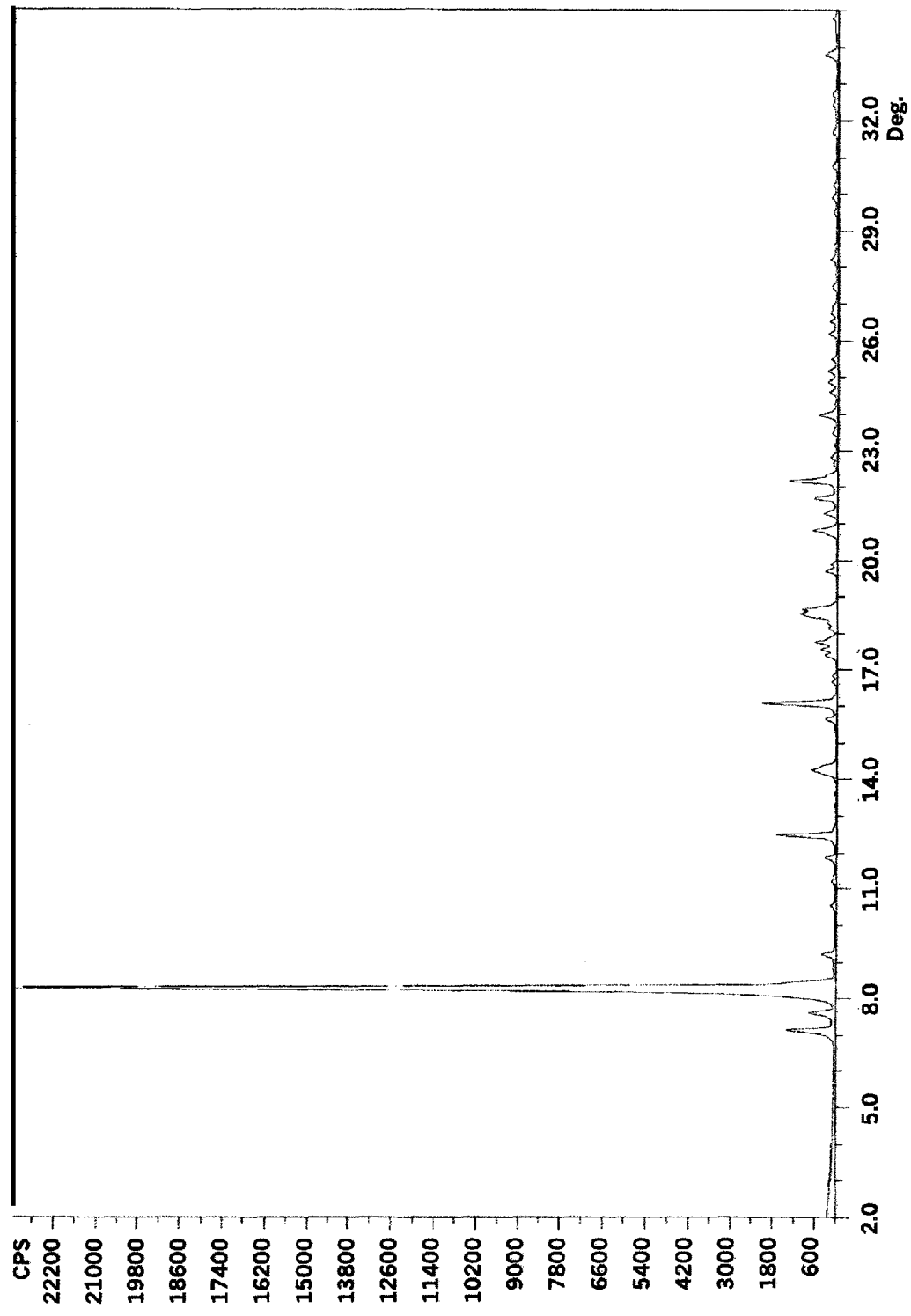
FIG. 4 shows the X-ray powder diffraction pattern of mycophenolate sodium adduct (hemisalt).
Figure 5:
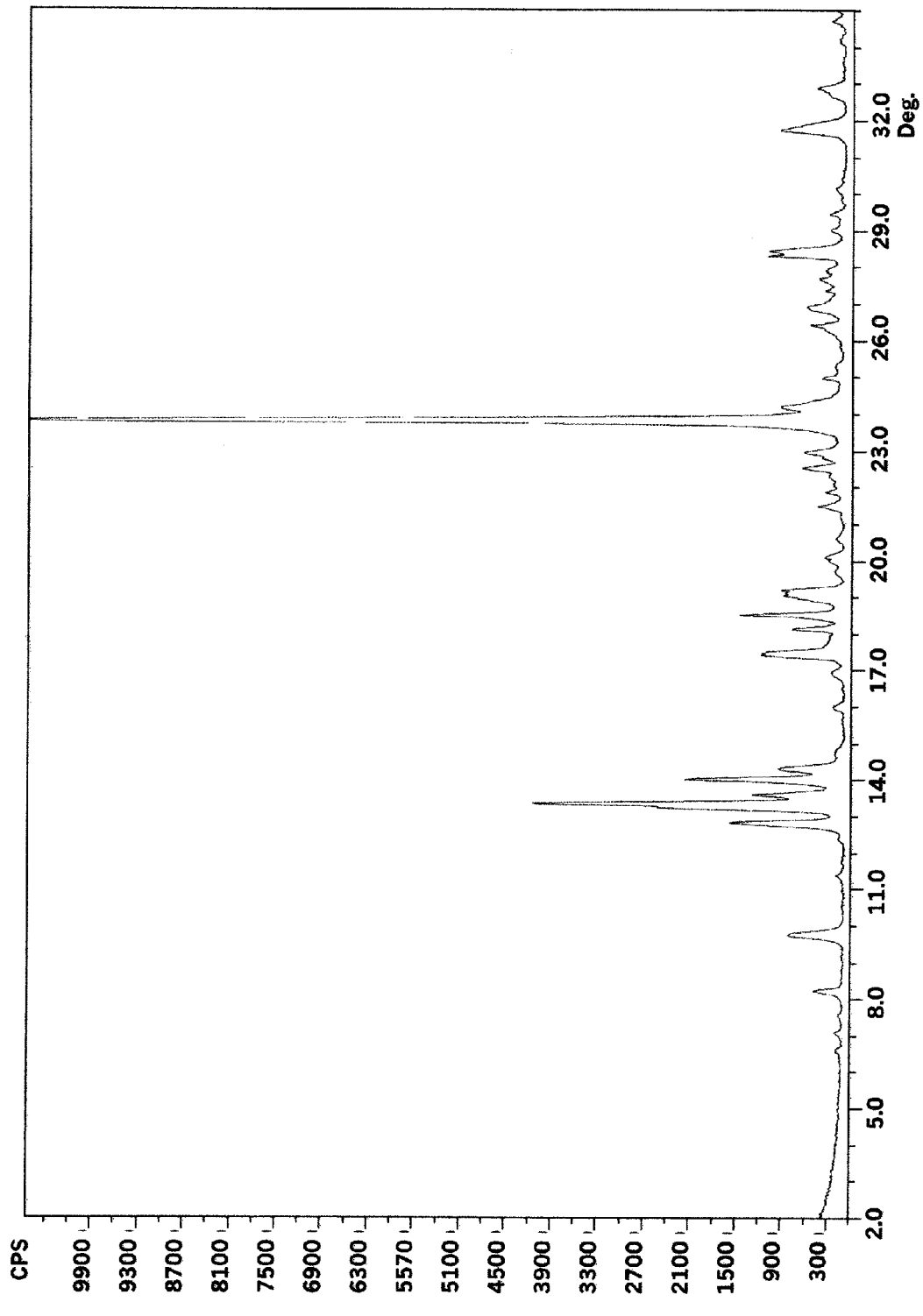
FIG. 5 shows the X-ray powder diffraction pattern of mycophenolate sodium methanol solvate.
Figure 6:
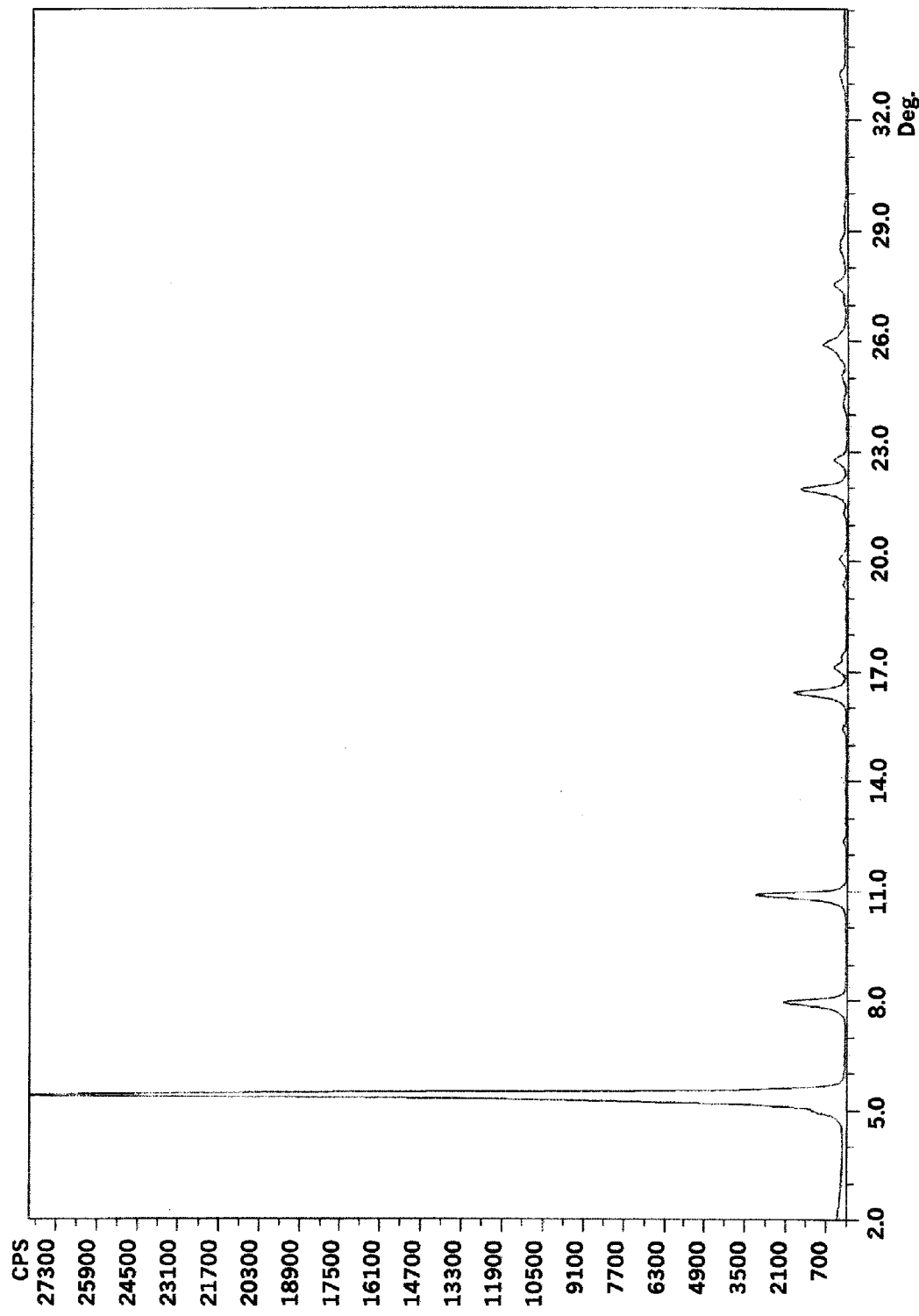
FIG. 6 shows the X-ray powder diffraction pattern of mycophenolate disodium salt, monohydrate.
Figure 7:
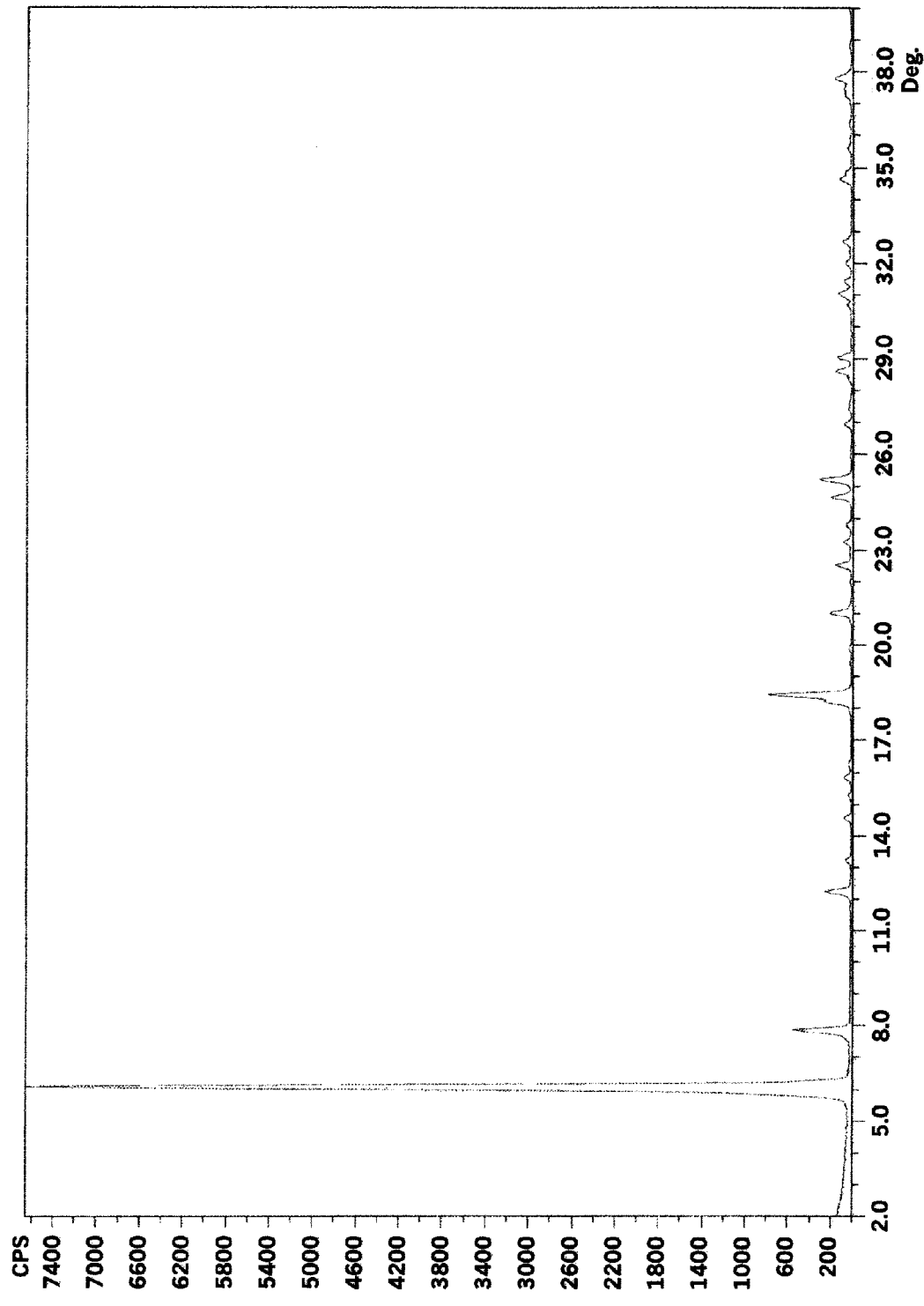
FIG. 7 shows the X-ray powder diffraction pattern of di-sodium salt II pentahydrate.
Figure 8:
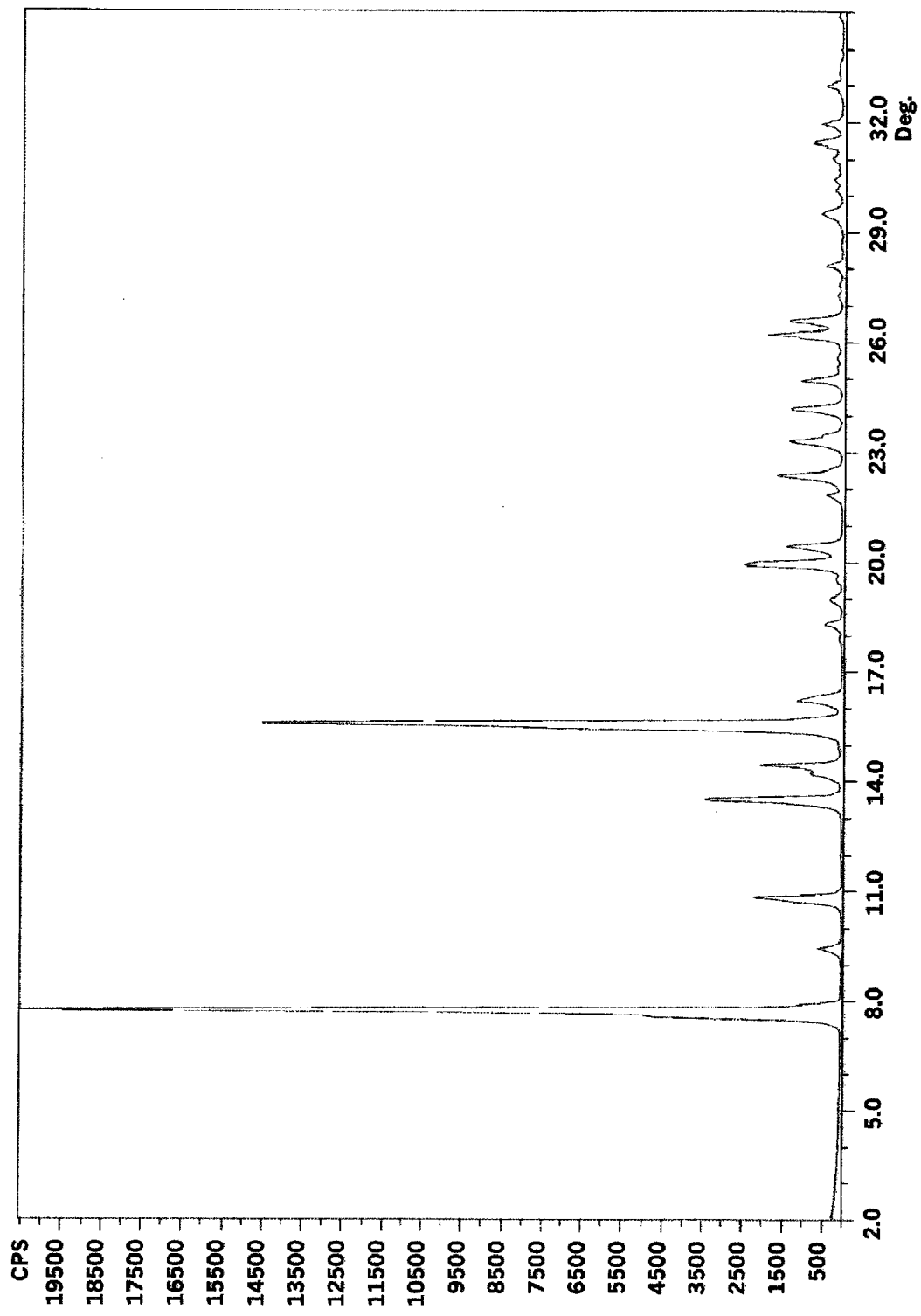
FIG. 8 shows the X-ray powder diffraction pattern of mycophenolic acid.
Figure 9:
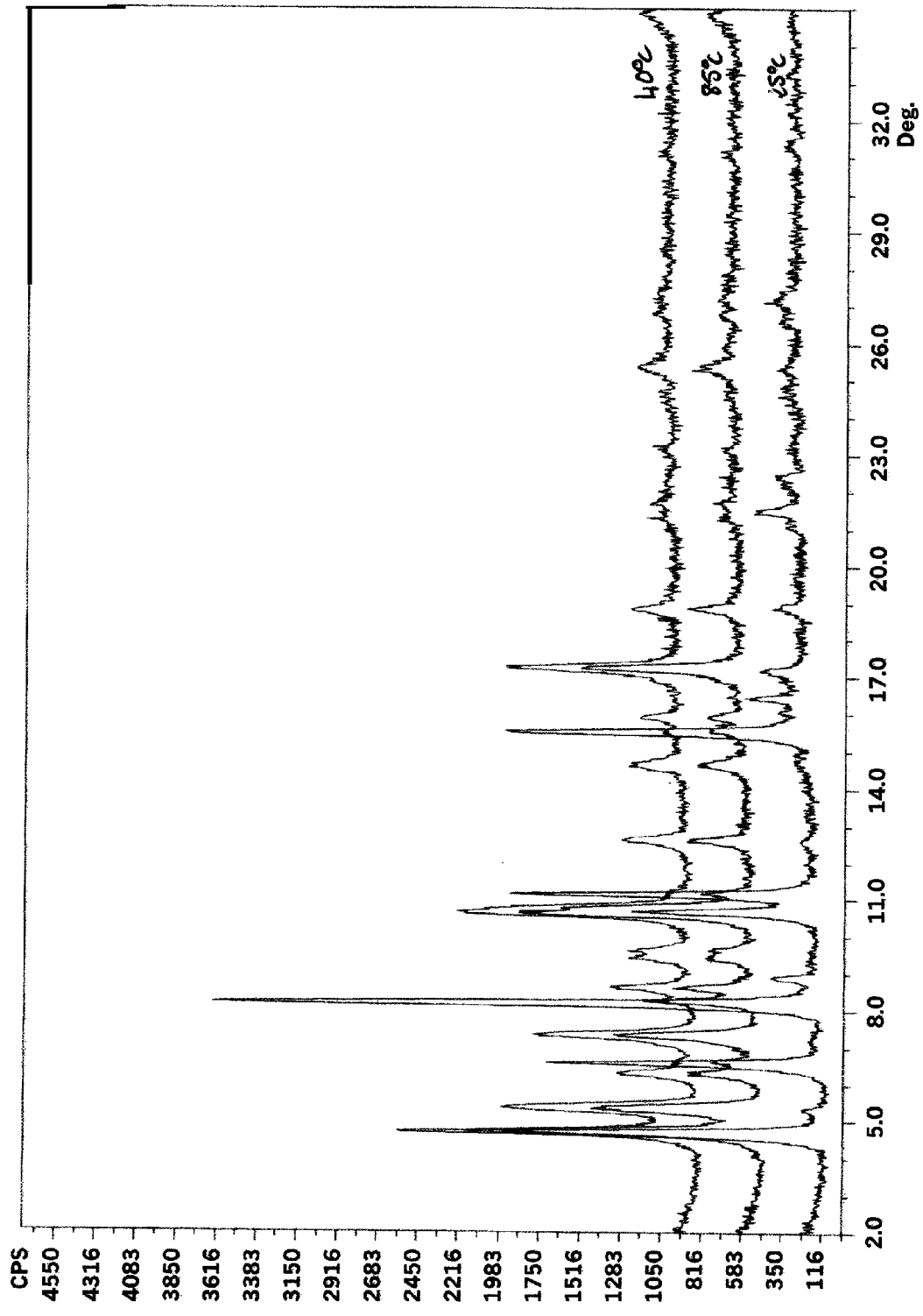
FIG. 9 shows the X-ray pattern at various temperatures of mycophenolate sodium hydrate Form B.
Figure 10:
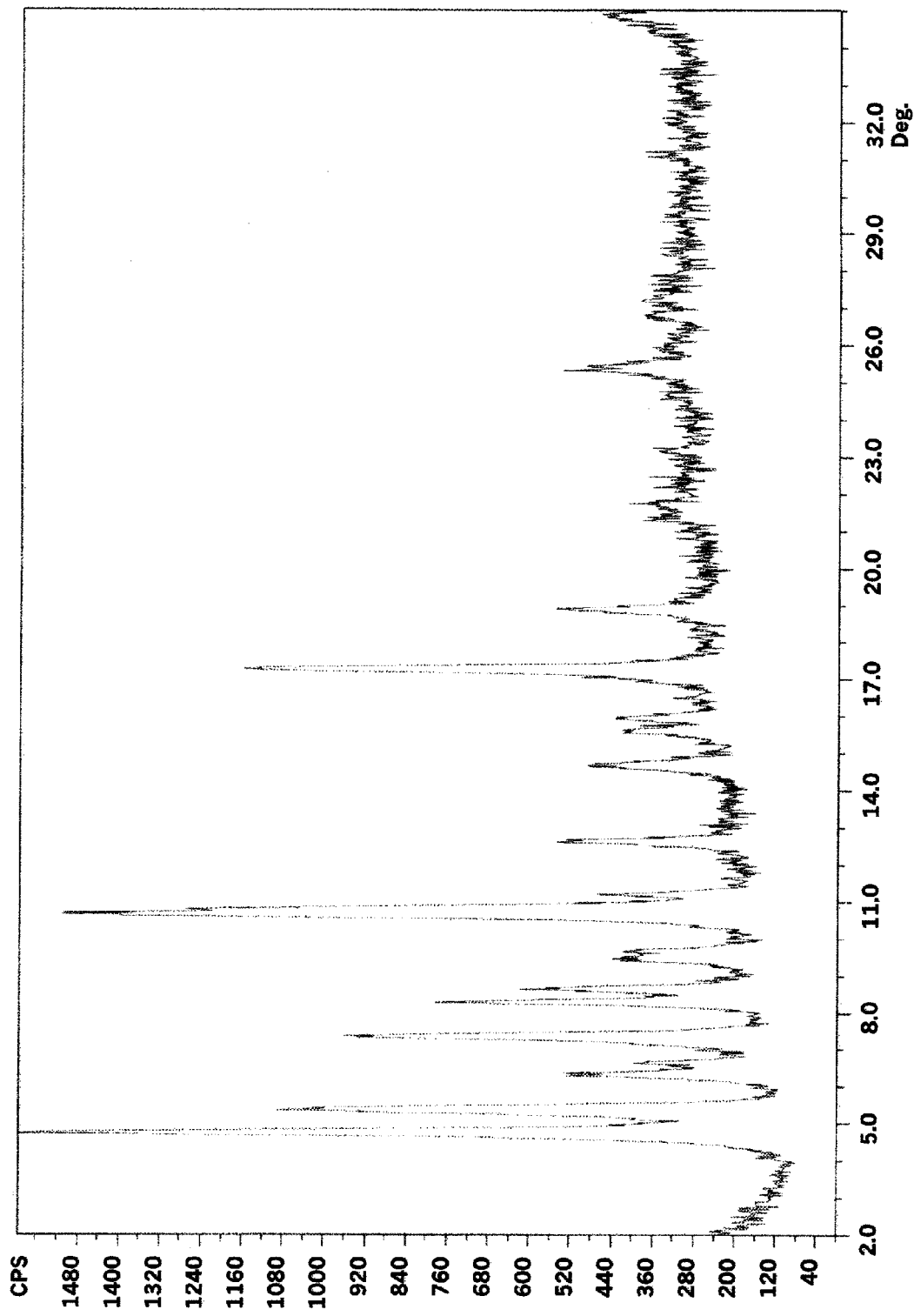
FIG. 10 shows the X-ray powder diffraction pattern of Form B.
Figure 11:
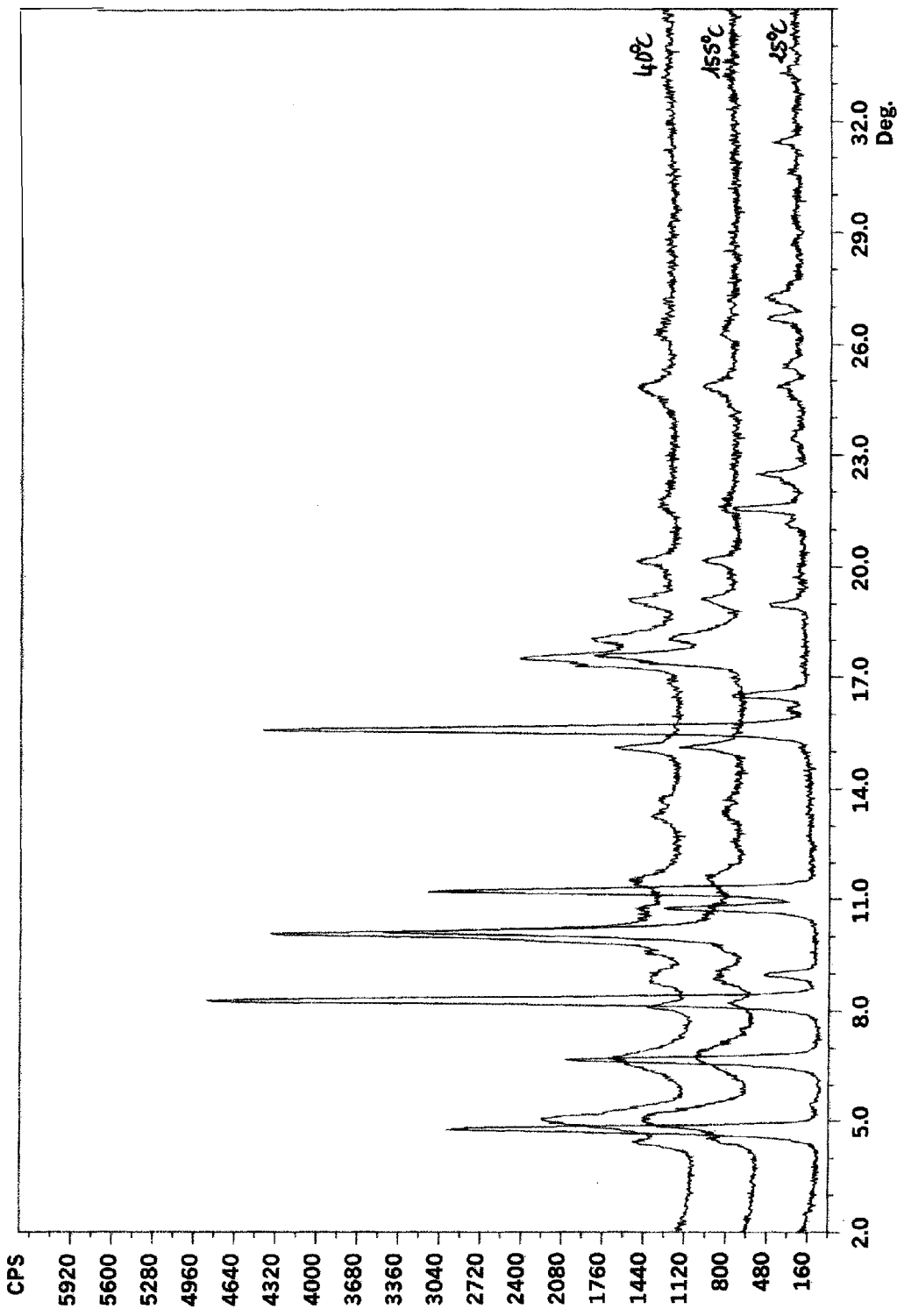
FIG. 11 shows The X-ray pattern at various temperatures for mycophenolate sodium hydrate Form C.
Figure 12:
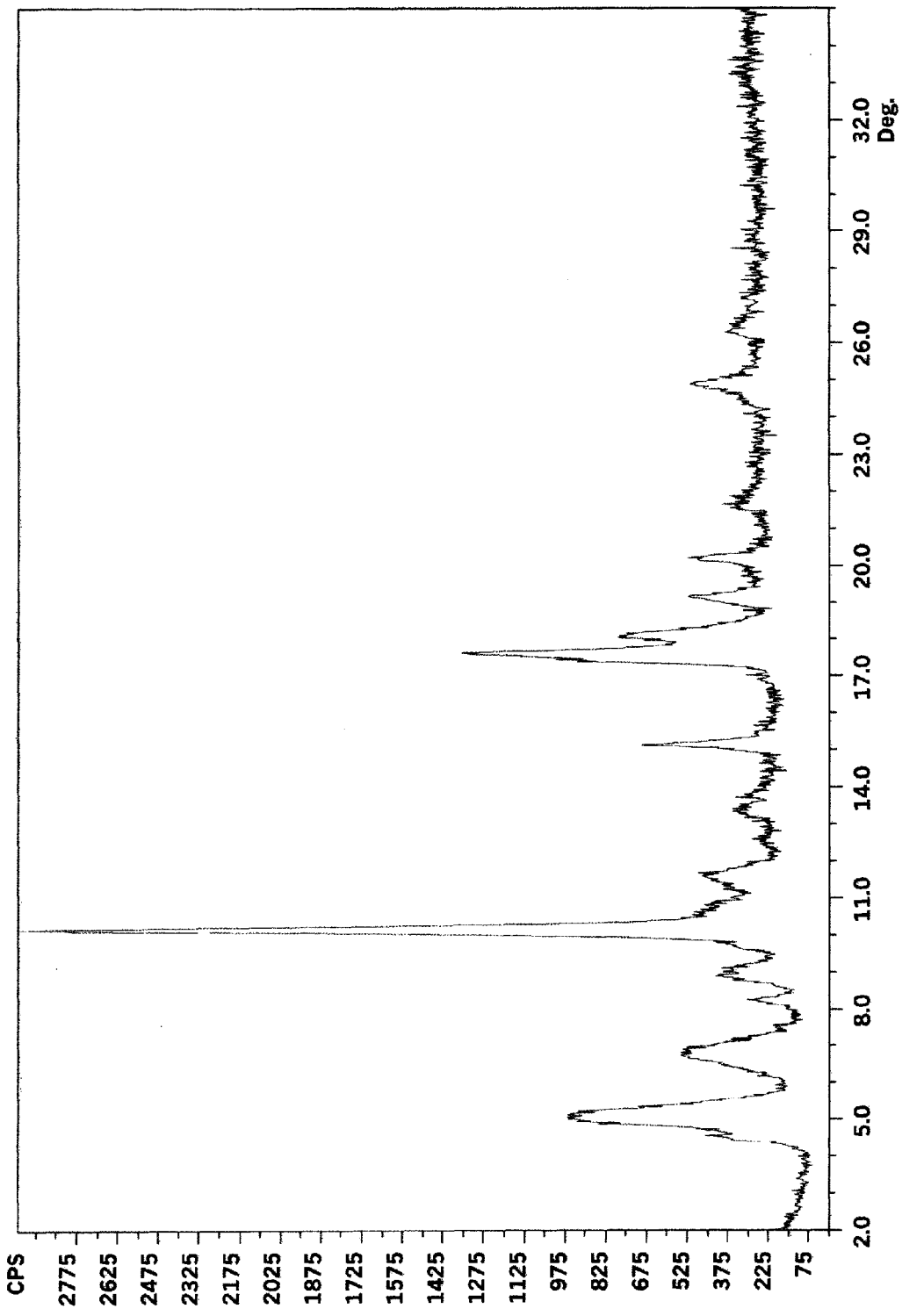
FIG. 12 shows the X-ray powder diffraction pattern of Form C.

The following Examples serve to illustrate the invention.

EXAMPLE 1

Fine long rods of mycophenolate mono-sodium salt, anyhdrate (mod. A) are obtained by crystallization from isopropanol, filtration and drying at 50° C. in a paddle dryer. The crystals have a mean length of 20-50 μm, a mean width of about 1 μm and a bulk density of about 180-200 kg/m³. The crystal habit of these crystals is modified as described in Examples 2 to 6.

EXAMPLES 2 TO 5

40 g of mycophenolate mono-sodium salt crystallized as described in Example 1 are suspended in 120 g of methanol/water in a mixing ratio of 95/5 in a stirred vessel. The suspension is oscillated at a mean temperature of 44° C. with an amplitude of +/−6° C. The period of one oscillation is 110 min, the number of oscillations is given in Table 1. The process temperature is controlled in a way that it performs a zigzag-curve over time.

240 g of ethanol are added and the suspension is cooled to 0° C. within 3 h. After filtration and drying in a rotary dryer, large compact crystals are obtained. The final bulk density is given in Table 1.

TABLE 1

|  | Ex. 2 | Ex. 3 | Ex. 4 | Ex. 5 |
| --- | --- | --- | --- | --- |
| number of oscillations | 5 | 6 | 10 | 16 |
| bulk density [kg/m³] | 280 | 310 | 380 | 490 |

Similarly, the mycophenolate mono-sodium salt may be suspended in methanol/water in another mixing ratio ranging between about 98:2 and 90:10.

EXAMPLE 6

20 g of mycophenolate mono-sodium salt crystallized as described in Example 1 are suspended in 60 g of methanol/water in a mixing ratio of 95/5 in a stirred vessel. The suspension is oscillated at a mean temperature of 44° C. with an amplitude of +/−6° C. The period of one oscillation is 160 min, the number of oscillations is 8. The process temperature is controlled in a way that it performs a sinus-curve over time.

180 g of ethanol are added during 180 min whereby the oscillation is continued. Then the suspension is cooled to 0° C. within 3 h. After 2 h, the crystals are filtered and dried in a rotary dryer. The final bulk density is 350 kg/m³.

EXAMPLE 7

| Component | amount in [mg] | amount in [mg] |
| --- | --- | --- |
| Mycophenolate sodium | 192.4 | 384.8 |
| Anhydrous lactose | 45.0 | 90.0 |
| Crospovidone | 32.5 | 65.0 |
| Povidone K30 PH | 20.0 | 40.0 |
| Maize Starch | 10.3 | 20.5 |
| Colloidal silicon dioxide | 6.6 | 13.2 |
| Magnesium stearate | 3.3 | 6.5 |
| Enteric coating: | | |
| Hypromellose phthalate HP50 | 42.0 | 65.0 |
| Titanium dioxide | 2.9 | 4.7 |
| Iron oxide yellow | 0.08 | 0.17 |
| Iron oxide red | — | 0.17 |
| Indigo carmine | 0.039 | — |

Mycophenolate sodium, Povidone® K30, silica, colloidal anhydrous are mixed, wet-granulated using ethanol 94%

(w/w), mixed with lactose anhydrous, maize starch, Crospovidone®, and magnesium stearate; and compressed to tablets.

The tablets are coated in a perforated pan coater with a solution of the coating ingredients in ethanol (with 5% isopropanol)/acetone.

The tablets have a hardness of 130 to 156 KN. Abrasion is less than 0.3%.

The invention claimed is:

1. Crystals of an acicular drug substance of a mycophenolate sodium salt and hydrates thereof with an aspect ratio of about 10:1 to 1:1 and a bulk density of above about 200 kg/m$^3$, an aspect ratio of about 10:1 to 1:1, or a bulk density of above about 200 kg/m$^3$.

2. A pharmaceutical composition in the form of tablets, comprising crystals of claim 1 in association with a pharmaceutically acceptable carrier.

3. Crystals according to claim 1 wherein the mycophenolate salt is mycophenolate sodium.

* * * * *

UNITED STATES PATENT AND TRADEMARK OFFICE
CERTIFICATE OF CORRECTION

PATENT NO.         : 8,008,511 B2
APPLICATION NO.    : 12/337663
DATED              : August 30, 2011
INVENTOR(S)        : Sabine Pfeffer et al.

It is certified that error appears in the above-identified patent and that said Letters Patent is hereby corrected as shown below:

Col. 13, lines 10 thru Col. 14, line 3 should read

1. Crystals of an acicular drug substance of a mycophenolate sodium salt and hydrates thereof with an aspect ratio of about 10:1 to 1:1 and a bulk density of above about 200 kg/m³, ~~an aspect ratio of about 10:1 to 1:1, or a bulk density of above about 200 kg/m³~~.

Signed and Sealed this
Eighteenth Day of October, 2011

David J. Kappos
*Director of the United States Patent and Trademark Office*